United States Patent
Shaikh

(10) Patent No.: US 6,722,368 B1
(45) Date of Patent: Apr. 20, 2004

(54) INTUBATION DEVICE

(75) Inventor: Amer Shaikh, London (GB)

(73) Assignee: Intavent Orthofix Limited (GB)

( * ) Notice: Subject to any disclaimer, the term of this patent is extended or adjusted under 35 U.S.C. 154(b) by 0 days.

(21) Appl. No.: 09/786,988
(22) PCT Filed: Sep. 15, 1999
(86) PCT No.: PCT/GB99/03070
§ 371 (c)(1), (2), (4) Date: Mar. 19, 2001
(87) PCT Pub. No.: WO00/16841
PCT Pub. Date: Mar. 30, 2000

(30) Foreign Application Priority Data

Sep. 19, 1998 (GB) .............................................. 9820358

(51) Int. Cl.⁷ .............................................. A61M 16/00
(52) U.S. Cl. ............................ 128/207.15; 128/207.14; 128/200.26
(58) Field of Search ....................... 128/207.15, 207.16, 128/207.17, 207.18, 200.26

(56) References Cited

U.S. PATENT DOCUMENTS

| | | | |
|---|---|---|---|
| 3,866,599 A | | 2/1975 | Johnson ................... 128/207.18 |
| 3,985,141 A | * | 10/1976 | Stanley et al. ........... 128/207.15 |
| 4,064,882 A | * | 12/1977 | Johnson et al. .......... 128/207.15 |
| 4,116,201 A | * | 9/1978 | Shah ......................... 128/207.15 |
| 4,150,676 A | | 4/1979 | Jackson .................... 128/207.15 |
| 4,178,940 A | * | 12/1979 | Au ............................. 128/207.15 |
| 4,270,529 A | * | 6/1981 | Muto ......................... 128/200.26 |
| 4,351,330 A | | 9/1982 | Scarberry ..................... 600/342 |
| 4,770,170 A | * | 9/1988 | Sato et al. ................. 128/205.24 |
| 5,513,627 A | * | 5/1996 | Flam ........................ 128/200.26 |
| 5,653,229 A | * | 8/1997 | Greenberg ............... 128/200.26 |
| 5,743,258 A | * | 4/1998 | Sato et al. ............... 128/200.26 |
| 5,746,202 A | * | 5/1998 | Pagan ....................... 128/200.26 |
| 6,095,144 A | * | 8/2000 | Pagan ....................... 128/207.14 |
| 6,152,136 A | * | 11/2000 | Pagan ....................... 128/207.14 |

FOREIGN PATENT DOCUMENTS

| | | |
|---|---|---|
| EP | 0 448 878 | 10/1991 |
| EP | 0 712 638 | 5/1996 |
| WO | WO95/06492 | 3/1995 |
| WO | WO95/23624 | 9/1995 |
| WO | WO95/33506 | 12/1995 |
| WO | WO97/48432 | 12/1997 |
| WO | WO98/23317 | 6/1998 |

* cited by examiner

Primary Examiner—Aaron J. Lewis
Assistant Examiner—Mital Patel
(74) Attorney, Agent, or Firm—Akerman Senterfitt

(57) ABSTRACT

An intubation device comprises an airway tube (10) a distal end of which is surrounded by an inflatable cuff (12) which is shaped and dimensioned to lie, in use, between the soft palate and the laryngeal inlet posteriorly of the palatopharyngeal folds. When inflated the cuff (12) has roughly the shape of the frustum of a four-sided pyramid with rounded corners and tapers away from its distal end. The distal end of the tube (10) is recessed ID into the distal end of the cuff so that the latter is an annular protrusion (13) adapted to straddle the upper region of but not to surround the elliptical epiglottis (14) and to fill the piriform fossae (15) on either side thereof.

11 Claims, 5 Drawing Sheets

INTUBATION DEVICE

This invention relates to an improved intubation device for use in assisting the breathing of a patient and in administering anaesthetics to a patient, for example during a surgical procedure.

To prevent asphyxiation it is essential to maintain a patent airway to the larynx but it is also essential to prevent penetration of blood and other secretions to the lungs. For purposes of maxillary, facial, oral, dental, nasal, ear and throat surgery it has therefore been common to use an endotracheal tube, which has an inflated cuff which seals the trachea below the vocal cords. However an endotracheal tube cannot be used without first inducing neuromuscular paralysis in the patient, as otherwise touching the vocal cords will induce a reflex spasm which will close the larynx.

International Patent Application publication No. WO 95/33506 and the British patent publications to which it refers disclose a laryngeal mask which, because it is located around the epiglottis and outside the laryngeal inlet, may be used without neuromuscular paralysis. However this mask is a relatively large object and because of its shape presents problems of location which give rise to dangers of injury to the patient. International Patent Application publication No. WO 95/06492 discloses an alternative to the laryngeal mask, the so-called COPA, which is located higher in the throat and which seals it by forcing forward the tongue and closing the naso-pharynx by lifting the soft palate. Both of these devices must be introduced orally, the laryngeal mask because it is too large to be introduced through the nose and the COPA not only for this reason but because it must close the back of the nose. Therefore both are unsuitable when access to the mouth is required and the COPA device is particularly unsuitable for operations on the back of the mouth or the throat, such as tonsilectomy, because its cuff projects into the oral cavity obscuring both the red tonsils and the uvula.

The principal object of the present invention is to improve upon prior art devices by providing a cuffed tube which although small enough to be introduced through the nose will effectively seal the throat above the epiglottis, at the same time providing access to the back of the mouth.

In accordance with one aspect of the present invention, there is provided an intubation device comprising an airway tube including a proximal end, a distal end and a wall where the airway tube is dimensioned for nasal insertion to introduce the tube into the throat of a patient. The intubation device also includes an inflatable cuff surrounding the distal end of the airway tube where the inflatable cuff has a generally flat distal surface, an anterior surface, and a generally flat postenor surface generally parallel with the airway tube. The generally flat distal surface forms an acute angle with the posterior surface and forms an obtuse angle with the anterior surface. The distal end of the airway tube is recessed into the distal surface of the inflatable cuff and the distal surface forms a distal protrusion beyond the airway tube. The inflatable cuff, when uninflated, is dimensioned to permit nasal insertion of the device into the throat of a patient and, when inflated is dimensioned and shaped to enter the vallecula and seat over an upper region only of the ellipical epiglottis and to seal the piriform fossae on either side thereof. The distal surface is adapted to seal against the posterior pharyngeal wall. The cuff reduces in cross-sectional area away from the distal protrusion such that when inflated the cuff will span the oro-pharynx in a region behind the palatopharyngeal folds below the soft palate and above the laryngeal inlet substantially without intrusion into the oral cavity.

It will of course be understood that the fact that the device of the invention can be introduced nasally in no way prevents its insertion orally if that is the preferred option in general airway management.

References to a "cuff" are used herein to denote both a balloon surrounding the tube and a tubular membrane sealed at opposite ends to the tube periphery.

When inflated the cuff is preferably a generally polyhedral body all the corners of which are rounded.

Preferably the plane of said annular protrusion forms an angle of approximately 45° with respect said longest side in the inflated condition of the cuff.

In a preferred embodiment the cuff when inflated has generally the shape of a frustum of a four-sided pyramid of which said longest side is the base, the plane of a proximal surface of the cuff being generally at right angles to the plane of the base.

Preferably the cuff is provided both with a one-way inflation valve and with a pressure-relief valve, the latter being preset to prevent pressure within the cuff rising above a predetermined value. The pressure-relief valve may be adjustable to vary the predetermined pressure within the cuff which will open the pressure-relief valve. The pressure-relief valve is desirable to prevent over expansion of the cuff, with consequent harm to the patient, which may occur during anaesthesia if anaesthetic gases migrate into the cuff through its membrane material.

The said valves are preferably in a common housing which is associated with a pilot balloon, the interior of the pilot balloon communicating with the interior of the cuff via an auxiliary line at least part of the length of which is within the wall of the tube.

When the device is to be introduced orally it may further comprise a combined bite-block and connector element insertable in a proximal end of the tube and an apertured mouth surround element which extends from opposite sides of the connector element, the aperture or apertures of the mouth surround element permitting insertion into the mouth of suction equipment alongside said tube when the mouth surround element extends over the mouth of a patient.

The mouth surround element may have an elliptical aperture in the centre of which is a circular component adapted to surround the combined bite-block and connector element.

Opposite ends of the mouth surround element are preferably engageable by opposite ends of an elastic head band, the connection between each end of the band and the mouth surround being by means of components which can be snapped off to permit quick removal of the mouth surround from the face.

A preferred embodiment of the invention will now be described with reference to the accompanying Drawings, in which.

Figure 1A:
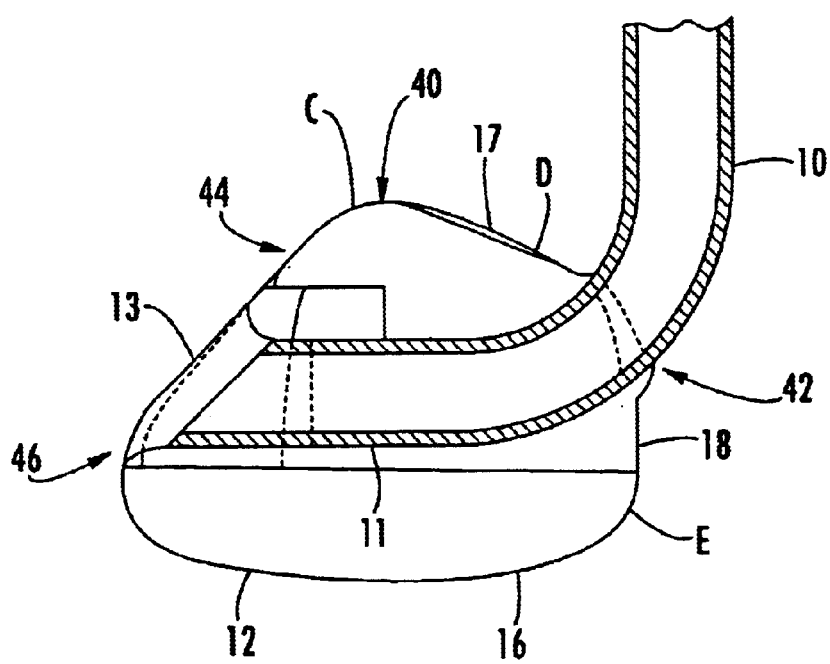
FIG. 1A illustrates a side perspective of a cross-sectional view showing the generally flat distal surface forming an acute angle with the posterior surface and forming an obtuse angle with anterior surface, and further, showing the airway tube bent through approximately a 90° angle in accordance with the inventive arrangements.

The device illustrated comprises an airway tube 10, a distal end region 11 of which is surrounded by an inflatable tube 12. The inflation medium may be of any known suitable kind, whether liquid or gaseous and is introduced to the cuff 12 via an auxiliary line 77 (FIG. 4A) which in known manner is embedded in the wall of the tube 10 and opens at one end to the interior of the cuff. At its other end the line 77 opens to a pilot balloon 78 equipped with two valves 19 and 20, the function of which will be described later.

Figure 2:
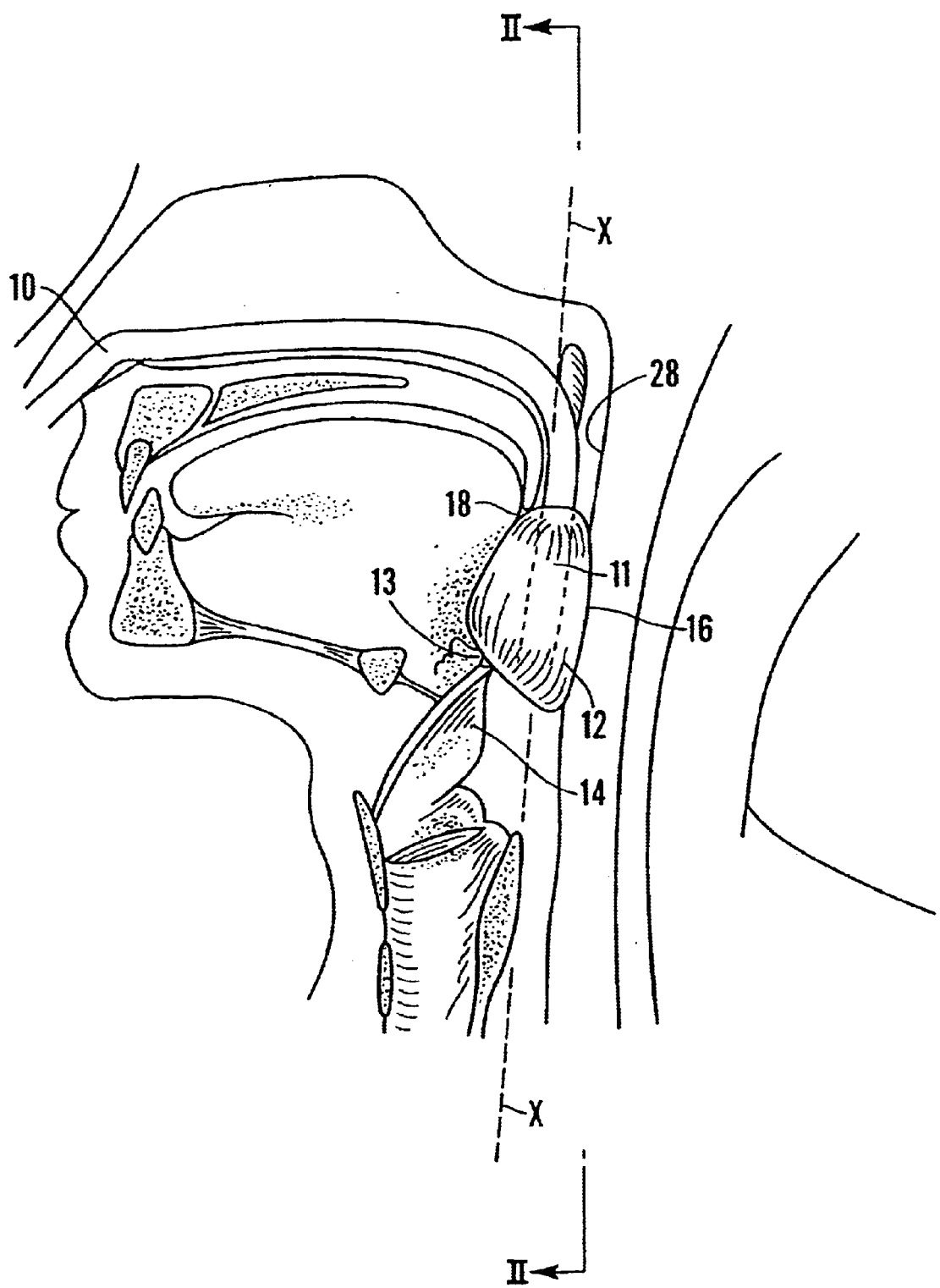
Figure 3:
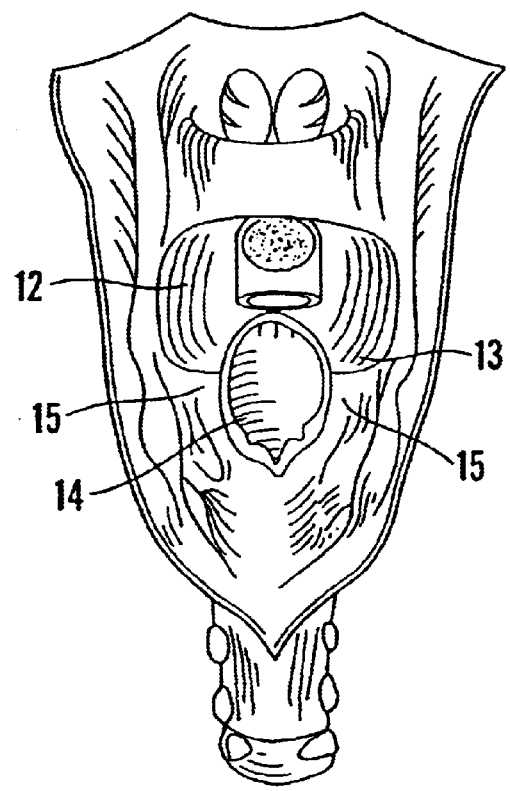

The dimensions both of tube 10 (or airway tube 10) and cuff 12 (or inflatable cuff 12) are such as to permit nasal intubation and cuff is shaped and dimensioned to fill the oro-pharynx, when suitably inflated, between the laryngeal inlet and the soft palate behind the palatopharyngeal folds. To achieve this, it has the shape illustrated in the FIGS. In particular the tube 10 is bent through approximately a 90° angle 42 adjacent to the inflatable cuff 12, as shown in FIG 1A. Further, the generally flat distal surface 44 (or the distal end 44 forms an acute angle 46 with the posterior surface 16 and forms an obtuse angle 40 with the anterior surface 17. Also, the distal end of the tube 10 is recessed in a distal surface 44 of the cuff 12, so that the end of the tube 1, is surrounded by an annular protrusion 13 of cuff 12. This annular protrusion is adapted to seat over the upper half only of the elliptical epiglottis 14, extending into the groove of the Vallecula and bilaterally into both Piriform Fossae, forming an effective seal up to an anterior margin level between the Hyoid bone and the Superior Cornua of the Thyroid cartilage (depending on anatomical vanations which occur with age and sex). Also to facilitate this, the plane 44 of the annular protrusion 13 forms and acute angle 46 of 45° or more with the plane of the longer side 16 of the cuff 12 which in use will press against the posterior pharyngeal wall. The effect of this is that in use of the device the plane 44 of the protrusion 13 will form an angle of 45° or less with the axis x—x of the throat (FIG. 2). In contrast to this longer side 16, the anterior side 17 forms an obtuse angle 40 with the generally flat distal surface 44. Additional, the cuff 12 is domed, the dome having a highest point near the annular protrusion 13 and tapering down toward the proximal end 18 of the cuff 12, so that the cuff 12 reduces in cross sectional area away from the annular protrusion 13.

Figure 1B:
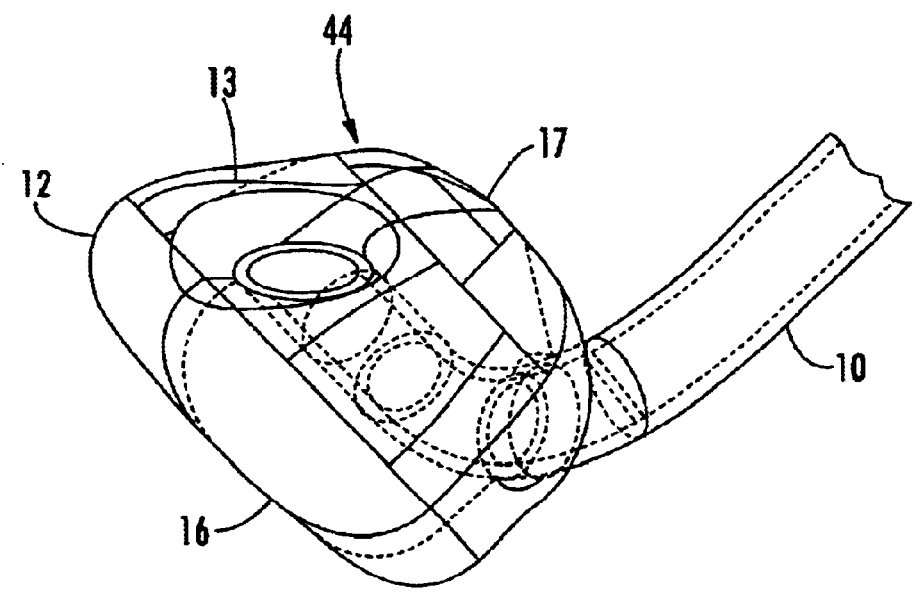
FIG. 1B illustrates a elevated perspective of a cross-sectional view of the distal end of the airway tube provided with a cuff in accordance with the inventive arrangements.

As will be seen most clearly from FIGS. 1A and 1B the inflated cuff has roughly the shape of the frustum of a four-sided pyramid of which side 16 represents the base and side 17 the frustum surface, although it will be understood that all corners are rounded and all the surfaces which connect them are slightly domed so that the cuff presents no straight edges potentially harmful to throat tissue. In use of the device surfaces D and E (FIG. 1A) sit below the soft palate and surface C protrudes into the arches on either side of the back of the tongue known as the palatopharyngeal folds from which the gelatinous vulva is suspended. This leaves the red tonsils open and available for removal. The relatively straight surface of longer side 16 presses against the posterior pharyngeal wall 28 (FIG. 2), helping to locate the device and prevent any tendency to rotate about a horizontal axis. The annular protrusion 13 is shaped and dimensioned to enter and locate over the Vallecula groove on top of the elliptical epiglottis and to extend into the gutter-like Piriform Fossae 15 on either side of the latter to provide a blood- and secretion-tight seal across the throat which will prevent such material reaching the larynx from the nose or mouth. It is to be noted that the device of the invention achieves this without surrounding the elliptical epiglottis in the manner of a laryngeal mask and consequently without deep penetration of the throat, without substantial displacement of the tongue and without closing or filling either the nasal or the oral cavity. These features and the relatively small size of the device reduce the dangers of damage to tissue present when using prior art devices.

Figure 4B:
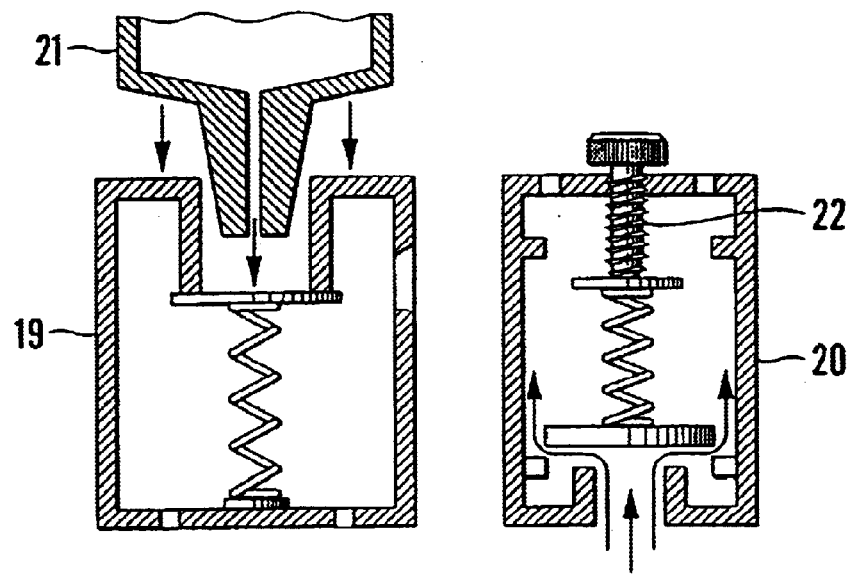
Figure 4A:
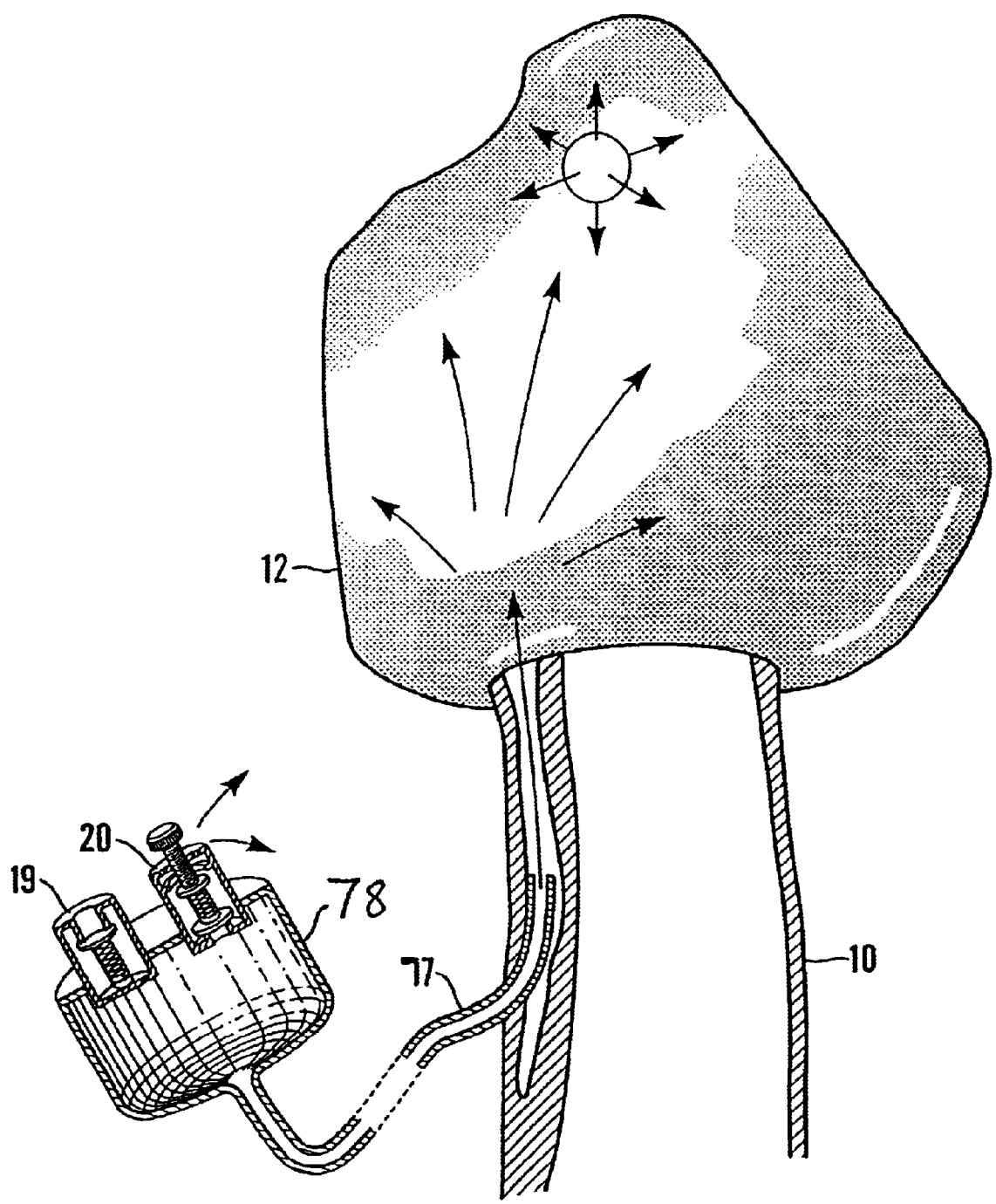

In use of the device of the invention first it is introduced into the throat with the cuff in a deflated condition, either through the nose or the mouth. Gas is introduced into the pilot balloon 78 through non-return valve 19, typically using a syringe 21 (FIG. 4B). The pressure relief valve 20 is also spring-biassed to the closed position, the loading of the spring and hence the setting at which the valve opens being adjustable by means of a screw 22. It is intended that the relief valve 20 should have a restricted gas escape passage such that excess pressure is relieved quite slowly, the resulting hiss or some auditory signal associated with the escaping gas alerting the operator to the existence of excess pressure.

Initially the cuff 12 is slightly over inflated (relative to the setting of the relief valve 20) so as to accommodate the cuff to the particular patient's throat. The pressure relief valve 20 opens to bring the pressure within cuff 12 down to the selected operating pressure to which valve 20 has been set by the screw 22. Thereafter if the cuff expands through diffusion into it of anaesthetic gases the pressure relief valve 20 will again open to reduce the excess pressure.

Figure 5A:
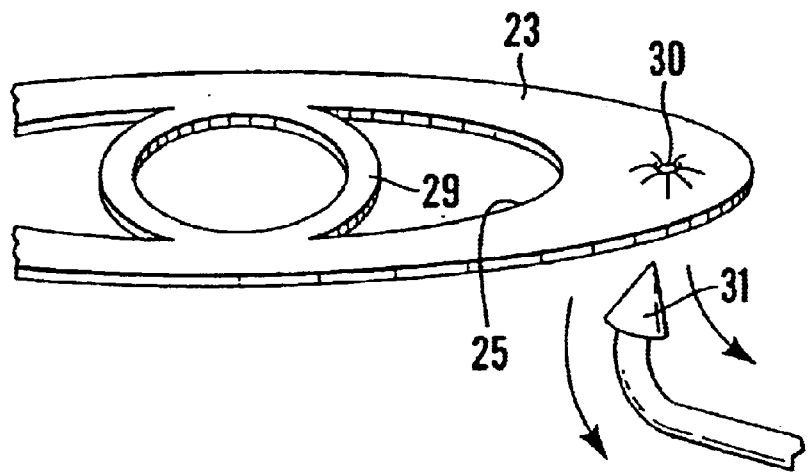
Figure 5B:
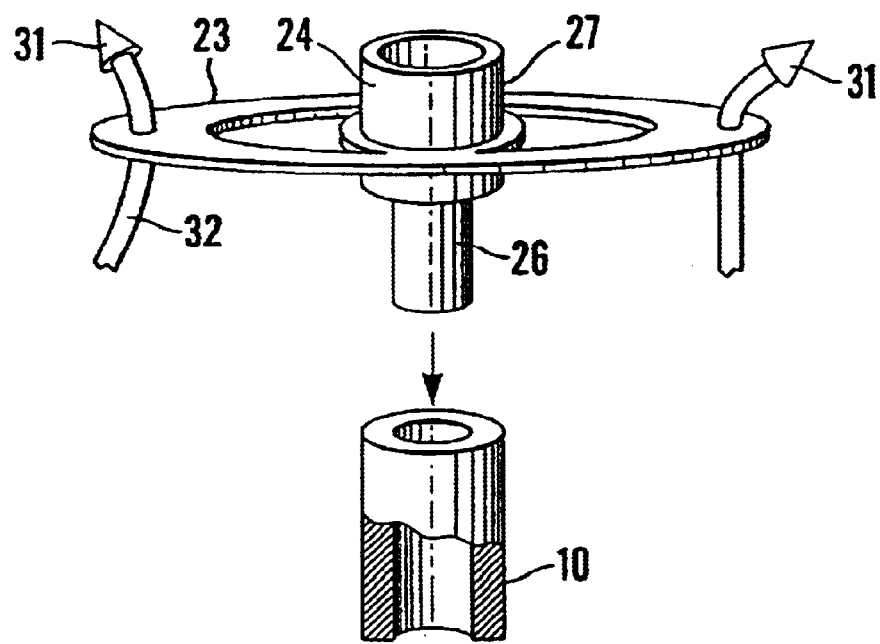

FIGS. 5A and 5B illustrate a face mouth surround 23 and a combined bite-block and connector element 24 which are used when the device of the invention is inserted orally. The mouth surround 23 has an elliptical opening 25 in the centre of which is located a circular element 29. Element 24 has a tubular bite-block component 26 insertable as a friction fit within the proximal end of the airway 10 and a relatively larger diameter connector component 27 adapted for connection to standard anaesthetic and breathing equipment. The circular component 29 is dimensioned to fit over the bite-block 26 and seat against the step between the latter and the connector component.

At opposite ends of the mouth surround 23 are small openings 30 through which can be pushed arrow-head-shaped formations 31 at opposite ends of an elastic head band 32. The head band 32 will pass round the head of the patient to hold the mouth surround 23 in front of the mouth, but the formations 31 are designed to snap off if subjected to unusual force for rapid removal of the mouth surround, and hence the tube 10, in the event of an emergency.

The elliptical opening 25 of the mouth surround 23 provides spaces on both sides of the connector 24 through which suction apparatus can be inserted into the mouth alongside the tube 10.

What is claimed is:

1. An intubation device, comprising:

an airway tube including a proximal end, a distal end and a wall, said airway tube being dimensioned for nasal insertion to introduce the tube into the throat of a patient; and an inflatable cuff surrounding said distal end of said airway tube, said inflatable cuff including a generally flat distal surface, an anterior surface, and a generally flat posterior surface generally parallel with said airway tube, said generally flat distal surface forming an acute angle with said posterior surface, and forming an obtuse angle with said antenor surface;

wherein said distal end of said airway tube is recessed into said distal surface of said inflatable cuff, said distal surface forming a distal protrusion beyond the airway tube.

wherein said inflatable cuff, when uninflated, is dimensioned to permit nasal insertion of the device into the throat of a patient and, when inflated, is dimensioned and shaped to enter the vallecula and seat over an upper region only of the elliptical epiglottis and to seat the piriform fossae on either side thereof, the distal surface being adapted to seal against the posterior pharyngeal wall; and wherein the cuff reduces in cross-sectional area away from said distal protrusion such that when inflated the cuff will span the oro-pharynx in a region behind the palatopharyngeal folds below the soft palate and above the laryngeal inlet substantially without intrusion into the oral cavity.

2. The device as claimed in claim 1, wherein when inflated said inflatable cuff is a generally polyhedral body having rounded corners.

3. The device as claimed in claim 1, wherein said generally flat distal surface forms an angle of approximately 45° with respect to said posterior surface in an inflated condition of said inflatable cuff.

4. The device as claimed in claim 1, wherein said inflatable cuff when inflated is generally shaped as a frustum of a four-sided pyramid having said posterior surface as the longest side of said frustum, a plane of a proximal surface of said inflatable cuff being generally at right angles to a plane of the posterior surface.

5. The device as claimed in claim 1, wherein said inflatable cuff is provided both with a one-way inflation valve and with a pressure-relief valve, the pressure-relief valve being preset to prevent pressure within said inflatable cuff remaining above a predetermined value.

6. The device as claimed in claim 5, wherein the pressure-relief valve is adjustable to vary a predetermined pressure value within said inflatable cuff which will open the pressure-relief valve.

7. The device as claimed in claim 6, wherein said one-way inflation valve and said pressure-relief valve are in a common housing which is associated with a pilot balloon an interior of the pilot balloon communicating with an interior of said inflatable cuff via an auxiliary line having a length, and wherein at least part of the length of the auxiliary line is within said wall of said airway tube.

8. The device as claimed in claim 1, further comprising a combined bite-block and connector element insertable in said proximal end of said airway tube and a mouth surround element having at least one aperture which extends from opposite sides of the connector element, the at least one aperture of the mouth surround element permitting insertion into the mouth of a patient of suction equipment alongside said airway tube when the mouth surround element extends over the mouth of the patient in use.

9. The device as claimed in claim 8, wherein the mouth surround element has an elliptical aperture having a circular component in a central portion of the aperture, and wherein the circular component is adapted to surround the combined bite-block and connector element.

10. The device as claimed in claim 9, wherein opposite ends of the mouth surround element are engageable by opposite ends of an elastic head band, a connection between each end of the band and the mouth surround element being by means of components which can be snapped off to permit quick removal of the mouth surround element from the face.

11. The device as claimed in claim 1, wherein said airway tube is bent through approximately a 90° angle adjacent to said inflatable cuff.

\* \* \* \* \*